United States Patent
At

(10) Patent No.: US 9,271,930 B2
(45) Date of Patent: Mar. 1, 2016

(54) DERMATOLOGICAL FOAMS OBTAINED FROM A GEL OR SUSPENSION CONTAINING ADAPALENE

(75) Inventor: Emmanuelle At, Antibes (FR)

(73) Assignee: GALDERMA RESEARCH AND DEVELOPMENT, Biot (FR)

( * ) Notice: Subject to any disclaimer, the term of this patent is extended or adjusted under 35 U.S.C. 154(b) by 0 days.

(21) Appl. No.: 13/997,164

(22) PCT Filed: Dec. 22, 2011

(86) PCT No.: PCT/FR2011/053159
§ 371 (c)(1),
(2), (4) Date: Aug. 28, 2013

(87) PCT Pub. No.: WO2012/085481
PCT Pub. Date: Jun. 28, 2012

(65) Prior Publication Data
US 2013/0338230 A1    Dec. 19, 2013

(30) Foreign Application Priority Data
Dec. 23, 2010    (FR) .................................... 10 61167

(51) Int. Cl.
| | | |
|---|---|---|
| A61K 31/19 | (2006.01) | |
| A61K 9/12 | (2006.01) | |
| A61K 8/04 | (2006.01) | |
| A61K 8/368 | (2006.01) | |
| A61K 9/00 | (2006.01) | |
| A61K 9/06 | (2006.01) | |
| A61K 9/10 | (2006.01) | |
| A61K 31/192 | (2006.01) | |
| A61K 47/10 | (2006.01) | |
| A61K 47/26 | (2006.01) | |
| A61K 47/32 | (2006.01) | |
| A61K 47/36 | (2006.01) | |
| A61K 47/38 | (2006.01) | |
| A61Q 19/00 | (2006.01) | |
| A61Q 19/10 | (2006.01) | |

(52) U.S. Cl.
CPC ................. *A61K 9/122* (2013.01); *A61K 8/042* (2013.01); *A61K 8/044* (2013.01); *A61K 8/046* (2013.01); *A61K 8/368* (2013.01); *A61K 9/0014* (2013.01); *A61K 9/06* (2013.01); *A61K 9/10* (2013.01); *A61K 31/192* (2013.01); *A61K 47/10* (2013.01); *A61K 47/26* (2013.01); *A61K 47/32* (2013.01); *A61K 47/36* (2013.01); *A61K 47/38* (2013.01); *A61Q 19/00* (2013.01); *A61Q 19/10* (2013.01)

(58) Field of Classification Search
USPC ........................................................ 514/557
See application file for complete search history.

(56) References Cited

U.S. PATENT DOCUMENTS

| | | | |
|---|---|---|---|
| 4,717,720 A * | 1/1988 | Shroot et al. ..................... 514/63 |
| 7,700,076 B2 * | 4/2010 | Tamarkin et al. ................ 424/47 |
| 8,937,098 B2 * | 1/2015 | Mallard et al. ................. 514/557 |
| 2005/0163731 A1 * | 7/2005 | Pelisson et al. ................. 424/59 |
| 2010/0143445 A1 * | 6/2010 | Pelisson et al. ............... 424/443 |

FOREIGN PATENT DOCUMENTS

| | | |
|---|---|---|
| WO | 03/075908 A1 | 9/2003 |
| WO | 2007/007198 A2 | 1/2007 |
| WO | 2008/007224 A2 | 1/2008 |
| WO | 2008/008397 A2 | 1/2008 |
| WO | 2009/068610 A1 | 6/2009 |

OTHER PUBLICATIONS

International Search Report mailed Feb. 29, 2012, by the European Patent Office as the International Searching Authority in corresponding International Application No. PCT/fr2011/053159.

* cited by examiner

*Primary Examiner* — Rei-Tsang Shiao
(74) *Attorney, Agent, or Firm* — Dentons US LLP

(57) ABSTRACT

Intermediate compositions and in particular gels and suspensions for a foam composition comprising adapalene are described. Also described, is the dermatological use of such compositions.

21 Claims, No Drawings

DERMATOLOGICAL FOAMS OBTAINED FROM A GEL OR SUSPENSION CONTAINING ADAPALENE

CROSS-REFERENCE TO PRIOR APPLICATIONS

This application is a National Stage of PCT/FR 2011/053159, filed Dec. 22, 2011, and designation the United States (published on Jun. 28, 2012, as WO 2012/085481 A1), which claims priority under 35 U.S.C §119 to FR 1061167, filed Dec. 23, 2010, each hereby expressly incorporated by reference in its entirety and each assigned to the assignee hereof.

The present invention relates to foam compositions based on adapalene, in particular as topical dermatological compositions, especially for treating dermatoses such as acne.

It is known practice to use retinoids for the topical treatment of various pathologies associated with the skin or mucous membranes, in particular acne.

However, the galenical forms commonly developed are in the form of aqueous gels or emulsions (lotions or creams), which are poorly suited to the treatment of acne.

The advantage of seeking to obtain a novel treatment that is effective on dermatological complaints in a stable composition affording good cosmeticity, enabling a single targeted application, and also a use that is pleasant for the patient, may thus be appreciated.

6-[3-(1-adamantyl)-4-methoxyphenyl]-2-naphthoic acid (referred to hereafter as adapalene) is a naphthoic acid derivative having retinoid and anti-inflammatory properties. This molecule has been the subject of development for the topical treatment of common acne and retinoid-sensitive dermatoses.

Adapalene is marketed under the brand name Differin® at a weight concentration of 0.1%, in the form of a solution referred to as an alcoholic lotion, an aqueous gel and a cream. These compositions are intended for treating acne. Patent application FR 2 837 101 describes, for its part, compositions of adapalene at a weight concentration of 0.3%, for treating acne.

One aim of the present invention is thus to provide novel foam compositions that are particularly suited to topical administration, comprising adapalene in dispersed form. These foam compositions are obtained from intermediate compositions in the form of gels or suspensions comprising the active agent.

The formulation in foam form containing a retinoid is advantageous for topical treatments, such as that of acne, since it allows an application of adapalene on the skin that is not only pleasant for the patient but also easy, unique and effective. Moreover, this type of formulation has very good cosmeticity for patients.

The majority of the formulation bases for obtaining a foam existing at the present time are in the form of emulsions.

Patent WO 2007/007198 describes compositions of foam type obtained from emulsions containing a retinoid. These compositions have a substantial proportion of organic vehicle representing from 2% to 50% of the total weight of the composition. This high content of organic vehicle is unsuitable for the treatment of acne since it gives a greasy feel.

Specifically, the compositions in foam form existing in the prior art thus have the following drawbacks:
the viscosity of the formulations is unsuitable for easy application. This gives the formulation poor efficacy;
the foams are largely obtained from emulsions. Now, emulsions are compositions that are rich in fatty phase, which are incompatible with the treatment of acne, which, on the contrary, requires refreshing, aqueous and non greasy compositions. These compositions leave a greasy feel on the skin after application.

The existing compositions in foam form therefore do not have all the properties required for the treatment of acne as described previously.

It thus turns out essential to develop a dermatological composition of foam type obtained from an intermediate composition in the form of a gel and/or a suspension for topical application which affords very good stability, a cosmetically acceptable non-greasy feel (absence of fatty phase), good maintenance of the active agent in dispersed form within the formulation, and a viscosity that enables easy application on the skin, targeted on lesions.

The compositions of foam type obtained from intermediate compositions of gel type according to the invention do not contain a fatty phase and have a viscosity of greater than 8000 cps after preparation at room temperature (25° C.) measured under the conditions defined in example 1 of the present patent application ("Example 1: Characterization of the intermediate formulations of gel and suspension type").

The compositions of foam type obtained from intermediate compositions of suspension type according to the invention do not contain a fatty phase and have a viscosity of between 8000 cps and 32 000 cps after preparation at room temperature (25° C.) measured under the conditions defined in example 1 of the present patent application ("Example 1: Characterization of the intermediate formulations of gel and suspension type").

Hereinbelow in the present patent application, the terms "intermediate composition", "composition of gel and/or suspension type", "composition in gel and/or suspension form", "intermediate formulation" and "formulation of gel and/or suspension type" will be used indifferently to denote the intermediate gel and/or suspension composition leading to the production of the foam composition according to the invention. The terms "composition" or "composition of foam type" or "foam" represent the final composition in foam form.

In the intermediate compositions according to the invention, the active agent is present in dispersed form.

The term "gel" means a semi-solid preparation containing a gelling agent which gives rigidity to a solution or to a colloidal dispersion (Lucinda Buhse et al., "Topical drug classification", International Journal of Pharmaceutics, 2005 (295), 101-112).

The term "suspension" means a liquid preparation containing solid particles dispersed in a liquid vehicle which is compatible for cutaneous application (CDER Data Standards Manual, version 008, Apr. 14, 1992). A liquid flows with little or no external forces and shows newtonian or pseudoplastic behavior (Lucinda Buhse et al., "Topical drug classification", International Journal of Pharmaceutics, 2005 (295), 101-112).

The Applicant has in particular prepared a foam from an intermediate composition of gel type comprising:
adapalene,
water,
at least one gelling agent and/or pH-independent gelling agent,
at least one surfactant,
at least one wetting agent,
optionally, a chelating agent,
optionally, at least one humectant and/or emollient,
optionally, one or more additives,
said adapalene being in dispersed form in said composition.

The Applicant has also prepared a foam from an intermediate composition of suspension type comprising:
adapalene,
water,
at least one gelling agent and/or pH-independent gelling agent,
at least one suspension agent and/or viscosity enhancer, at least one surfactant,
at least one wetting agent,
optionally, a chelating agent,
optionally, at least one humectant and/or emollient,
optionally, one or more additives,
said adapalene being in dispersed form in said composition.

The present invention comprises adapalene.

In the gels and suspensions according to the invention, adapalene is used at concentrations of between 0.001% and 10% by weight relative to the total weight of the intermediate composition, preferably between 0.01% and 5%, more preferentially between 0.05% and 0.5% and most preferentially from 0.1% to 0.3% by weight relative to the total weight of the intermediate composition.

Advantageously, the particle size of the adapalene is such that at least 90% numerically of the particles and preferably at least 90% numerically of the particles have a diameter less than 10 μm and at least 99% numerically of the particles have a diameter less than 50 μm, the particle sizes preferably being measured by optical microscopy.

Preferably, the adapalene is in dispersed form.

According to the invention, the term "active agent in dispersed form" means an active principle in the form of solid particles, suspended in a given vehicle. Such particles preferably have a size greater than 10 μm.

The suspending power for the dispersed active agent such as adapalene of our compositions of gel and suspension type is optimized by means of the addition of at least one gelling agent and in the presence or absence of at least one suspension agent and/or viscosity enhancer.

The aqueous phase of the gel or of the suspension may be present in a content of between 40% and 90% by weight and preferably between 65% and 85% by weight relative to the total weight of the intermediate composition.

The gelling agent(s) and/or pH-independent gelling agent(s) present in the gel or suspension have the role of increasing the viscosity of the aqueous phase. This makes it possible especially to improve the stabilization of this phase and its binding nature, which leads both to good homogeneity of the distribution of the active agent in the intermediate composition and to the production of foams having the desired texture and stability. As non limiting example, the gelling agent(s) and/or pH-independent gelling agent(s) may be chosen especially from:

"electrolyte-insensitive" carbomers sold, as nonlimiting examples, under the name Carbopol Ultrez-20®, Carbopol 1382® or Carbopol ETD 2020® by the company Noveon, and acrylates/C10-30 alkyl crosspolymer sold under the name Pemulen TR-1® or Pemulen TR-2® by the company Noveon;

polysaccharides, with non limiting examples including the xanthan gum sold under the name Xantural 180® by the company Kelco or Satiaxane UCX911® by the company Cargill, the guar gum sold under the name N-Hance® by the company IMCD, the locust bean gum sold under the name Viscogum® by the company Cargill, gum tragacanth and extracts of quince seeds; alginates such as the sodium alginate sold under the name Satialgine® by the company Cargill;

modified starches such as the modified potato starch sold under the name Structure Solanace® or mixtures thereof;

celluloses and derivatives thereof, for instance the hydroxyethylcellulose sold under the name Natrosol 250HHX® by the company IMCD, the methylcellulose sold under the name Benecel® by the company IMCD, the carboxymethylcellulose sold under the name Blanose 7H4F® by the company IMCD, the hydroxypropylmethylcellulose sold under the name Methocel E4M® by the company Dow Chemicals, and the hydroxypropylcellulose sold under the name Klucel HF® by the company IMCD;

polyvinyl alcohol, for instance the polyvinyl alcohol 40-88® sold by the company Merck;

the Polyquaternium family, for instance the Polyquaternium-10® sold under the name Celquat SC-240C® by the company National Starch;

acrylic polymers coupled to hydrophobic chains, such as the PEG-150/decyl/SMDI copolymer sold under the name Aculyn 44® (polycondensate comprising at least, as components, a polyethylene glycol containing 150 or 180 mol of ethylene oxide, decyl alcohol and methylenebis(4-cyclohexyl isocyanate) (SMDI), at 35% by weight in a mixture of propylene glycol (39%) and water (26%));

polyacrylamides such as the acrylamide/sodium acryloyldimethyltaurate copolymer/isohexadecane/polysorbate 80 mixture sold under the name Sepineo P600® (or Simulgel 600PHA®) by the company SEPPIC, the polyacrylamide/C13-14 isoparaffin/laureth-7 mixture, for instance the product sold under the name Sepigel 305® by the company SEPPIC, the hydroxyethylacrylate/sodium acryloyldimethyltaurate copolymer mixture sold under the name Sepinov EMT 100 by the company SEPPIC; and mixtures of these compounds.

The gelling agent and/or pH-independent gelling agent as described above may be used at preferential concentrations ranging from 0.1% to 10% by weight and more preferentially ranging from 0.2% to 5% by weight relative to the total weight of the intermediate composition.

As preferred gelling agents we can mention polysaccharides such as xanthan gum (Xantural 180®) and guar gum (N-Hance®), celluloses such as hydroxyethylcellulose (Natrosol 250HHX®), polyacrylamides such as the acrylamide/sodium acryloyldimethyltaurate copolymer/isohexadecane/polysorbate 80 mixture (Sepineo P600® (or Simulgel 600PHA®)) and the hydroxyethyl acrylate/sodium acryloyldimethyltaurate copolymer mixture (Sepinov EMT 10®)).

The suspension agent(s) present in the suspension have the role of maintaining in suspension the active agent present in the intermediate compositions without, however, increasing the viscosity. Examples that may be mentioned include:

the cellulose family, including, inter alia, microcrystalline cellulose and sodium carboxymethylcellulose sold under the name Avicel CL-611® by the company FMC Biopolymer;

the silicas family, including, inter alia, Aerosil 200® Pharma and Aerosil R972® sold by the company Evonik;

the polysaccharides family, including, inter alia, *Sclerotium rolfsii* sold under the name Amigel® by the company Alban Muller, the xanthan gum-locust bean gum combination sold under the name XPV-SG 600® by the company Cargill;

the carrageenans family, in particular divided into four main families: κ, λ, β, ω, such as the Viscarin® products (nonlimiting examples include Viscarin GP-379NF® and Viscarin GP-209NF®) and the Gelcarin® products (a nonlimiting example is Gelcarin GP-379NF®) marketed by the company IMCD;

the clays family, including, inter alia, magnesium aluminum silicate such as Veegum K® sold by the company Lavollée Chimie or bentones such as Veegum HS® sold by the company Lavollée Chimie;

the salts family, including, inter alia, the sodium chloride sold by the company Merck;

and mixtures thereof.

The suspension agent and/or viscosity enhancer as described above may be used at preferential concentrations ranging from 0.1% to 10% by weight and more preferentially ranging from 0.2% to 5% by weight relative to the total weight of the intermediate composition.

As preferred suspension agent and/or viscosity enhancer we can mention microcrystalline cellulose and sodium carboxymethylcellulose sold under the name Avicel CL-611®, carrageenans, for instance Viscarin GP-209NF®, clays, for instance Veegum HS®, and polysaccharides, for instance Amigel®.

The gels and suspensions of the present invention contain surfactants, that are amphiphilic molecules, which will allow to form the foam and to stabilize it (A. Arzhavitina, "Foams for pharmaceutical and cosmetics application", International Journal of Pharmaceutics, 394 (2010), 1-17).

Indeed, surfactants are amphiphilic compounds which bear a hydrophobic part that has affinity for oil and a hydrophilic part that has affinity for water, thus creating a link between the two phases. The polarity of the surfactant is defined by the HLB (hydrophilic/lipophilic balance).

A high HLB indicates that the hydrophilic fraction is predominant, and, conversely, a low HLB indicates that the lipophilic part is predominant. By way of example, HLB values greater than about 10 correspond to hydrophilic surfactants.

Surfactants may be classified, according to their structure, under the "ionic" generic terms (anionic, cationic or amphoteric) or "nonionic". Nonionic surfactants are surfactants that do not dissociate into ions in water and are thus insensitive to pH variations.

The surfactants present in the intermediate composition provide a surface modification to interfaces of liquid/gas type, which ensures the formation of the foam (Dominique Langevin, "Aqueous foams: a field of investigation at the frontier between chemistry and physics", ChemPhysChem, 2008 (9), 510-522) and stabilizes the film surrounding each foam bubble (Tim Kealy, Alby Abram, Richard Buchta, "The rheological properties of pharmaceutical foam: implications for use", International Journal of Pharmaceutics, 2008 (355), 67-80).

Non limiting examples of anionic surfactants that may be mentioned include sodium, ammonium or triethanolamine lauryl sulfates (the sodium lauryl sulfate marketed under the name Texapon K12 P PH® by the company Cognis), sodium, magnesium, ammonium or TEA (triethylamine) laurylethersulfates (the sodium laureth sulfate sold under the name Texapon N70® by the company Cognis), the sodium lauroyl sarcosinate marketed under the name Protelan LS9011® by the company Zschimmer & Schwarz, sodium olefin sulfonates, sulfoacetates, sulfosuccinates, sodium taurates, and sodium cocoyl glutamate & disodium cocoyl glutamate sold under the name Amisoft CS-22® by the company Ajinomoto.

Nonlimiting examples of cationic surfactants that may be mentioned include quaternary ammoniums, alkylpyridinium chlorides, alkylammonium saccharinates and aminoxides.

Nonlimiting examples of amphoteric surfactants that may be mentioned include betaines and derivatives thereof, for instance cocamidopropylbetaine sold under the name Amonyl 380BA® by the company SEPPIC, cocoylbetaine sold under the name Amonyl 265BA® by the company SEPPIC or Dehyton AB 30® by the company Cognis, and disodium cocoamphoacetate sold under the name Rewoteric AM2 C NM® by the company Evonik.

Nonlimiting examples of nonionic surfactants that may be mentioned include sorbitan esters such as POE(20) sorbitan monooleate, marketed under the name Tween 80®, POE(20) sorbitan monostearate, marketed under the name Tween 60®, sorbitan monostearate marketed under the name Span 60® by the company Uniqema, glycerol esters such as the glycerol monostearate marketed under the name Cutina GMSVPH® by the company Cognis, polyethylene glycol esters such as PEG-6 isostearate marketed under the name Olepal Isostéarique® by the company Gattefossé, fatty alcohol ethers such as POE(21) stearyl ether marketed under the name Brij 721® by the company Uniqema or Ceteareth-20 marketed under the name Eumulgin B2PH® by the company Cognis, polyoxyethylene glycol esters such as glyceryl stearate and PEG-100 stearate marketed under the name Arlacel 165 Flakes® by the company Uniqema, PEG 6 stearate and PEG 32 stearate marketed under the name Tefose 1500® by the company Gattefossé, sucroesters such as sucrose laurate marketed under the name Surfhope D-1216® or Surfhope C1215L® by the company Gattefossé, or the mixture of aqua (and) sucrose laurate (and) alcohol marketed under the name Sisterna L700® by the company Gattefossé, PEG-40 hydrogenated castor oil marketed under the name Eumulgin HRE40PH® by the company Cognis, decyl glucoside marketed under the name Oramix NS10® by the company SEPPIC, and caprylyl capryl glucoside marketed under the name Oramix CG110® by the company SEPPIC.

Irrespective of its nature, the surfactant as described above is preferably included in a content of between 0.2% and 15% by weight and preferably between 0.5% and 10% by weight relative to the total weight of the intermediate composition.

To obtain a foam with optimum properties, the surfactants that are particularly preferred are chosen from anionic surfactants (Texapon N70® and Protelan LS9011®), amphoteric surfactants (Amonyl 380BA® and Amonyl 265BA®) and nonionic surfactants (Tween 80®, Surfhope C1215L®, Sisterna L700®, Oramix NS10® and Eumulgin HRE40PH®).

The composition of gel or suspension type according to the invention also comprises at least one wetting agent. The role of wetting agents is to reduce the surface tension and to allow greater spreading of the liquid. A wetting agent that may preferentially have an HLB from 10 to 14 is used, without this list being limiting. Among the wetting agents that may be used according to the invention, mention may be made of compounds from the Poloxamer family, including Poloxamer 124 sold under the name Synperonic PE/L44® by the company Uniqema or Lutrol L44® sold by the company BASF, Poloxamer 182 sold under the name Synperonic PE/L62® by the company Uniqema or Lutrol L62® by the company BASF, and compounds of the glycols family, including propylene glycol, dipropylene glycol, propylene glycol dipelargonate, lauroglycol and ethoxydiglycol.

Preferably, wetting agents are in liquid form so as to be readily incorporated into the composition of gel or suspension type without it being necessary to heat it.

The wetting agent as described above may be used at preferential concentrations ranging from 0.05% to 10% by weight and more preferentially ranging from 0.1% to 8% by weight relative to the total weight of the intermediate composition.

The particularly preferred wetting agent is propylene glycol and Lutrol L44® sold by the company BASF.

Among the chelating agents, nonlimiting examples that may be mentioned include ethylene diamine tetra-acetic acid (EDTA), diethylene triamine penta-acetic acid (DTPA), ethylene diamine-di(O-hydroxyphenyl acetic)acid (EDDHA), hydroxy-2-ethylene diamine triacetic acid (HEDTA), ethyldiamine-di(O-hydroxy-p-methylphenyl)acetic acid (EDDHMA) and ethylene diamine-di(5-carboxy-2-hydroxyphenyl)acetic acid (EDDCHA).

The chelating agent as described above may be used at preferential concentrations ranging from 0% to 1.5% by weight and more preferentially ranging from 0% to 1% by weight relative to the total weight of the intermediate composition. When the chelating agent is present in the composition, its concentration is preferably comprised between 0.01% and 1%.

A preferred chelating agent that may be mentioned is ethylene diamine tetra-acetic acid (EDTA) sold in particular under the name Titriplex III®.

The composition of gel or suspension type according to the invention may also contain humectants, the role of which is to moisturize the skin and to facilitate the application of the formulation. Humectants and/or emollients that are preferentially used, without this list being limiting, include compounds such as glycerol ("glycerin") and sorbitol, sugars (for example glucose or lactose), PEGs (for example Lutrol E400), urea, amino acids (for example serine, citrulline, arginine, asparagine or alanine). These agents are taken alone or in combination in the composition.

The humectant and/or emollient as described above may be used at preferential concentrations ranging from 0% to 20% by weight and more preferentially ranging from 0 to 15% by weight relative to the total weight of the intermediate composition. When the humectant and/or emollient is present in the composition, its concentration is preferably comprised between 0.01% and 15%.

A preferred humectant and/or emollient that may be mentioned is glycerol.

The intermediate compositions of the invention may also optionally comprise any additive normally used in the cosmetic or pharmaceutical field, such as neutralizing agents of common mineral or organic acid or base type, sunscreens, antioxidants, fillers, electrolytes, preservatives, dyes, fragrances, essential oils, cosmetic active agents, moisturizers, vitamins, essential fatty acids, sphingolipids, self-tanning compounds, skin-calmative and skin-protecting agents, propenetrating agents, or a mixture thereof. Needless to say, a person skilled in the art will take care to select this or these optional additional compound(s), and/or their quantity, such that the advantageous properties of the composition according to the invention are not, or are not substantially, impaired.

These additives as described above may be used at preferential concentrations ranging from 0% to 20% by weight and more preferentially ranging from 0 to 15% by weight relative to the total weight of the intermediate composition. When the additive is present in the composition, its concentration is preferably comprised between 0.01% and 15%.

A person skilled in the art will take care to select the excipients constituting the intermediate compositions according to the invention according to the desired galenical form and such that the advantageous properties of the composition according to the invention are respected.

The invention thus relates to a pharmaceutical composition based on adapalene, characterized in that it is in the form of a foam obtained from an intermediate composition of gel or suspension type, especially for a topical application intended for treating acne.

More particularly, the invention relates to a pharmaceutical composition characterized in that it is in the form of a foam obtained from an intermediate composition of gel or suspension type, said composition comprising, on a weight basis relative to the total weight of the composition:
  between 60% and 98% by weight and preferentially between 80% and 96% by weight, relative to the total weight of the composition, of a gel or a suspension,
  between 2% and 40% by weight and preferentially between 4% and 20% by weight, relative to the total weight of the composition, of at least one propellant gas.

In one particular embodiment according to the invention, the intermediate composition in gel form comprises (percentage expressed on a weight basis relative to the total weight of the composition of gel type):
  (a) 0.001% to 10% and preferentially from 0.01% to 5% of adapalene;
  (b) 40% to 90% of water and preferentially from 65% to 85% of water;
  (c) 0.1% to 10% and preferentially from 0.2% to 5% of at least one gelling agent and/or pH-independent gelling agent for the aqueous phase;
  (d) 0.2% to 15% and preferentially from 0.5% to 10% of at least one surfactant;
  (e) 0.05% to 10% and preferentially from 0.1% to 8% of at least one wetting agent;
  (f) 0% to 1.5% and preferentially from 0% to 1% of a chelating agent;
  (g) 0% to 20% and preferentially from 0% to 15% of at least one humectant and/or emollient;
  (h) 0% to 20% and preferentially from 0% to 15% of one or more additives;
  said adapalene being in dispersed form in said gel.

In another particular embodiment according to the invention, the intermediate composition in suspension form comprises (percentage expressed on a weight basis relative to the total weight of the composition of suspension type):
  (a) 0.001% to 10% and preferentially from 0.01% 5% of adapalene;
  (b) 40% to 90% of water and preferentially from 65% to 85% of water;
  (c) 0.1% to 10% and preferentially from 0.2% to 5% of at least one gelling agent and/or pH-independent gelling agent for the aqueous phase;
  (d) 0.1% to 10% and preferentially from 0.2% to 5% of at least one suspension agent and/or viscosity enhancer;
  (e) 0.2% to 15% and preferentially from 0.5% to 10% of at least one surfactant;
  (f) 0.05% to 10% and preferentially from 0.1% to 8% of at least one wetting agent;
  (g) 0% to 1.5% and preferentially from 0% to 1% of a chelating agent;
  (h) 0% to 20% and preferentially from 0% to 15% of at least one humectant and/or emollient;
  (i) 0% to 20% and preferentially from 0% to 15% of one or more additives;
  said adapalene being in dispersed form in said suspension.

According to a preferred embodiment, the invention relates to a pharmaceutical composition based on adapalene, characterized in that it is in the form of a foam obtained from an intermediate composition of gel or suspension type which comprises:
  between 80% and 96% by weight, relative to the total weight of the composition, of a gel or a suspension,
  between 4% and 20% by weight, relative to the total weight of the composition, of at least one propellant gas,
  said gel comprising (percentage expressed on a weight basis relative to the total weight of the composition of gel type):
  (a) 0.01% to 5% of adapalene;
  (b) 65% to 85% of water;

(c) 0.2% to 5% of at least one gelling agent and/or pH-independent gelling agent for the aqueous phase;
(d) 0.5% to 10% of at least one surfactant;
(e) 0.1% to 8% of at least one wetting agent;
(f) 0% to 1% of a chelating agent;
(g) 0% to 15% of at least one humectant and/or emollient;
(h) 0% to 15% of one or more additives;
said adapalene being in dispersed form in said gel,
said suspension comprising (percentage expressed on a weight basis relative to the total weight of the composition of suspension type):
(a) 0.01% to 5% of adapalene;
(b) 65% to 85% of water;
(c) 0.2% to 5% of at least one gelling agent and/or pH-independent gelling agent for the aqueous phase;
(d) 0.2% to 5% of at least one suspension agent and/or viscosity enhancer;
(e) 0.5% to 10% of at least one surfactant;
(f) 0.1% to 8% of at least one wetting agent;
(g) 0% to 1% of a chelating agent;
(h) 0% to 15% of at least one humectant and/or emollient;
(i) 0% to 15% of one or more additives;
(j) 4% to 20% of at least one propellant gas;
said benzoyl peroxide being in dispersed form in said suspension.

The invention also relates to the use of the novel composition of foam type as described previously in cosmetics and dermatology.

By virtue of the pronounced activity of adapalene in the fields of cell differentiation and proliferation, the compositions of the invention are particularly suitable for use in the following therapeutic fields:

1) for treating dermatological complaints associated with a keratinization disorder relating to cell differentiation and proliferation, especially for treating common acnes, comedonal acnes, polymorphous acnes, acnes rosacea, nodulocystic acnes, acne conglobata, senile acnes, and secondary acnes such as solar acne, medication-related acne or occupational acne, and hidradenitis suppurativa;
2) for treating other types of keratinization disorders, especially ichthyosis, ichthyosiform conditions, Darier's disease, palmoplantar keratoderma, leukoplakia and leukoplakiform conditions, and cutaneous or mucous (oral) lichen;
3) for treating other dermatological complaints related to a keratinization disorder with an inflammatory and/or immunoallergic component, and especially all forms of psoriasis whether cutaneous, mucous or ungual, and even psoriatic rheumatism, or cutaneous atopy, such as eczema, or respiratory atopy or alternatively gingival hypertrophy; the compounds may also be used in certain inflammatory complaints not presenting a keratinization disorder, such as folliculitis;
4) for treating all dermal or epidermal proliferations, whether benign or malignant, and whether of viral origin or not, such as common warts, flat warts, molluscum contagiosum and verruciform epidermodysplasia, oral or florid papillomatosis, and proliferations that may be induced by ultraviolet radiation, especially in the case of actinic keratosis;
5) for combating sebaceous function disorders, such as the hyperseborrhea of acne or simple seborrhea;
6) in the treatment of dermatological complaints with an immunological component;
7) in the treatment of dermatological complaints associated with an inflammation or infection of the tissues surrounding the hair follicle, especially caused by microbial colonization or infection, especially impetigo, seborrheic dermatitis, folliculitis or sycosis barbae, or involving any other bacterial or fungal agent.

The compositions or gels and suspensions according to the invention are particularly suitable for preventively or curatively treating common acne.

The compositions according to the invention also find an application in cosmetics, in particular for the treatment of acne-prone skins and for combating the greasy appearance of the skin or the hair.

Preferentially, said compositions according to the invention are administered topically.

A subject of the invention is also a process for preparing a composition of gel or suspension type as described previously.

The process for preparing the intermediate composition of gel or suspension type according to the invention comprises, by way of example, the following steps:

Step a: Preparation of the Active Phase:
Mixing of purified water and of the active ingredient (adapalene) with at least one wetting agent until said adapalene is fully dispersed, so as to obtain the active phase;

Step b: Preparation of the Aqueous Phase
Purified water and the gelling agent(s) and/or the pH-independent gelling agent(s) (with the exception of polyacrylamide), the hydrophilic surfactant(s) and optionally the suspension agent(s) and/or viscosity enhancer(s), the chelating agent, the preservative(s), the stabilizing agent(s) and the humectant(s) and/or emollient(s) are placed in a beaker with stirring, if necessary with heating.

Step c: Preparation of the Gel or Suspension
The active phase obtained in step a) is then introduced with stirring into the aqueous phase.

Step d: Addition of Polyacrylamide (Optional)
Polyacrylamide is introduced into the gel or suspension with stirring. The stirring is maintained until perfect homogeneity.

Step e: Neutralization Step (Optional)
The gelling-agent neutralizer is introduced if necessary into the gel or suspension.

Step f: Water Adjustment (Optional)
If necessary, a water adjustment is performed.

The additives, if present in the gel or the suspension, are added to the aqueous phase.

According to yet another specific aspect, a subject of the invention is a process of preparing a composition in foam form based on adapalene, by mixing a gel or suspension with at least one propellant gas.

Foams are defined as a dispersion of a gas in a liquid or a solid (A. Arzhavitina, "Foams for pharmaceutical and cosmetics application", International Journal of Pharmaceutics, 394 (2010), 1-17).

The European pharmacopea 6th edition 2010 describes a "medicated foam" as being a preparation formed by the dispersion of a large volume of gas in a liquid preparation generally containing one or more active ingredients, at least one surfactant ensuring their formation, and various other excipients.

The American pharmacopea USP Chapter 1151 lists foams in the section "Aerosol foam". This is a composition containing one or more active ingredients, one or more surfactants, aqueous or non-aqueous liquids, and propellants.

The compositions in foam form of the present invention are obtained by introducing the intermediate composition of gel and/or suspension type into an aerosol container containing at least one propellant gas under pressure. The aerosol is constituted of three components "Pharmaceutical Dosage forms, USP 1151":

the leaktight case;
the valve for stoppering and for making the container in communication with the atmosphere to dispense the product;
the diffuser or pushbutton comprises the valve aperture and allows to modulate the flow rate.

By liberating the formulation of gel or suspension type from the container by means of the pushbutton, a foam is obtained.

The aerosol container used in the context of this embodiment is preferably a container of shaving foam spray type, namely a closed container under pressure, comprising an outlet nozzle connected to the gel or suspension and containing at least one propellant gas, a valve and a pushbutton suitable for dispensing the foam.

The aerosol thus differs from certain pump sprayers that act only by the action of a mechanical spring (absence of propellant gas). It should be noted that an aerosol always contains a propellant that flushes out and disperses the product (Martini M. C., Esthétique-cosmétique, volume 2, "Cosmétologie", Editions Masson, Paris, 2002).

The "propellant gases" that may be used in the present invention are of two types: compressed gases, liquefied gases.

Compressed gases are gaseous at room temperature. Examples that may be mentioned include nitrogen, carbon dioxide and nitrous oxide, and mixtures thereof.

Liquefied gases are liquid at room temperature. Examples that may be mentioned include butane, propane and isobutane, and mixtures thereof.

The propellant gases used according to the present invention are used in proportions ranging from 2% to 40% and preferentially ranging from 4% to 20% by weight of the composition.

According to a particular aspect, the aerosol containers for dispensing a foam, comprising a gel or suspension and at least one propellant gas under pressure, constitute another specific subject of the present invention.

The invention and the advantages arising therefrom will emerge more clearly from the following implementation examples. These examples are, however, in no way limiting.

Examples of preparation of intermediate formulations of gel or suspension type, and examples of compositions of foam type according to the invention, are thus described below. Similarly, the tests for characterizing the intermediate compositions and the foams are also defined.

EXAMPLE 1

Characterization of the Intermediate Compositions of Gel and Suspension Type

The physical stability of the intermediate formulations of gel or suspension type is controlled by a macroscopic and microscopic observation, conserved at room temperature (RT) and 40° C. after T+1 month or T+2 months or T+3 months.

At room temperature and 40° C., the macroscopic observation allows ensuring the physical integrity of the products.

At room temperature, the microscopic observation allows to evaluate the quality of dispersion of the active agent. Adapalene is observed in fluorescent light.

Characterization of the gel and of the suspension is completed by a viscosity measurement and by establishing a rheological profile.

Measurement of the apparent viscosity of the gel and of the suspension is done using Brookfield RVDVII+ and LVDVII+ viscometers at room temperature (25° C.).

The viscosity ranges that are measurable with these two types of Brookfield viscometer are as follows:
RVDVII+ viscometer: 100 cP-40 McP
LVDVII+ viscometer: 15 cP-6 McP This apparent viscosity measurement yields information regarding the viscosity of the gel and of the suspension at rest (in the packaging).

The establishment of the rheological profile of the gel and of the suspension allows to describe the rheological properties of the formulation, especially its flow threshold.

For the flow threshold measurement, a Haake VT550 rheometer with an SVDIN measuring spindle is used.

The rheograms are established at 25° C. and at an imposed speed of 0 to 100 s$^{-1}$. The viscosity values are noted at the shear values and at constant shear speed of 4 s$^{-1}$, 20 s$^{-1}$ and 100 s$^{-1}$ ($\gamma$), and by measuring the shear stress. The term "flow threshold" ($\tau_0$ expressed in Pascals) means the force (minimum shear stress) required to overcome the cohesion forces of Van der Waals type and to bring about the flow. The flow threshold is assimilated to the value found at the shear speed of 4 s$^{-1}$.

The chemical stability is determined by an HPLC assay of the adapalene.

The results are expressed as a percentage relative to the Label Claim (LC) (theoretical content of adapalene).

These physical and chemical tests will allow to ensure the good stability over time of the various gels and suspensions and thus of the foams obtained according to the invention.

EXAMPLE 2

Characterization of the Foams

The physical stability of the foams obtained is also characterized by means of the tests presented below:

Determination of the organoleptic characteristics (aspect, color, odor),
Characterization of the texture (thick, fluid, greasy, non-greasy),
Characterization of the spreading capacity (classified from 1 (easy spreading) to 5 (very difficult spreading)),
The quality of the foam leaving the container is evaluated according to a classification on a scale from 1 to 5, with "1" representing a foam with fine bubbles and "5" representing a foam with large bubbles,
The foam density measurement is performed according to the protocol described in the European Pharmacopea 6th edition 2010:
Protocol: Maintain the container at a temperature of 25° C. for at least 24 hours. While avoiding heating the container, fit a rigid tube 70 mm to 100 mm long and with an inside diameter of about 1 mm onto the pushbutton, shake the container to homogenize the liquid phase, and expel 5 ml to 10 ml of foam. Tare a flat-bottomed crystallizing dish with a volume of about 60 ml and a height of about 35 mm. Place the extremity of the rigid tube in the angle at the bottom of the crystallizing dish, and, to fill it uniformly, press the pushbutton while effecting a circular motion. After total expansion of the foam, level it off by scraping off the excess using a blade. Weigh. Determine the mass of the same volume of water R by filling the same crystallizing dish with water R. The foam density is equal to the ratio: m/e m=mass of the foam sample, in grams
e=mass of the same volume of water R, in grams
Take three measurements. None of the individual values differs from the mean value by more than 20%.

The foam expansion time is determined according to the protocol described in the European Pharmacopea 6th edition 2010:

Protocol: The apparatus consists of a 50 ml burette, with an inside diameter of 15 mm, with graduations of 0.1 ml, fitted with a 4 mm one-way tap. The graduation corresponding to 30 ml is at 210 mm at least from the axis of the tap. The low part of the burette is connected, via a plastic tube with a maximum length of 50 mm and an inside diameter of 4 mm, to the foam-generating container fitted with a pushbutton adapted to this connection. Maintain the container at a temperature of 25° C. for at least 24 hours. While avoiding heating it, shake the container to homogenize the liquid phase, and expel 5 ml to 10 ml of foam. Connect the pushbutton to the outlet of the burette. Press the pushbutton and introduce, in one go, an amount of foam of about 30 ml. Close the tap, simultaneously start the chronometer and read the volume of foam contained in the burette. Read then every ten seconds the volume that increases up to the maximum volume. Take three measurements. None of the times necessary to obtain the maximum volume is greater than 5 minutes.

These tests will allow ensuring the good stability over time of the various foams obtained.

EXAMPLE 3

Formulation of Gel Type Containing 0.1% Adapalene

| Constituents | Concentration (%) |
| --- | --- |
| Adapalene | 0.10 |
| Guar gum | 2.50 |
| Citric acid | 0.30 |
| Sodium laureth sulfate | 2.50 |
| Cocamidopropylbetaine | 5.00 |
| Glycerol | 5.00 |
| Ethylene diamine tetraacetic acid | 0.05 |
| Propylene glycol | 4.00 |
| Poloxamer 124 | 0.20 |
| Purified water | qs 100% |

EXAMPLE 4

Formulation of Gel Type Containing 0.1% Adapalene

| Constituents | Concentration (%) |
| --- | --- |
| Adapalene | 0.30 |
| Sodium acryloyldimethyltaurate copolymer/isohexadecane/polysorbate 80 | 3.00 |
| Polysorbate 80 | 8.00 |
| Aqua (and) sucrose laurate (and) alcohol | 2.00 |
| Glycerol | 4.00 |
| Ethylene diamine tetraacetic acid | 0.05 |
| Sodium docusate | 0.05 |
| Propylene glycol | 5.00 |
| Poloxamer 124 | 0.20 |
| Purified water | qs 100% |

EXAMPLE 5

Formulation of Gel Type Containing 0.1% Adapalene

| Constituents | Concentration (%) |
| --- | --- |
| Adapalene | 0.10 |
| Hydroxyethyl acrylate/sodium acryloyldimethyltaurate copolymer | 2.00 |
| Decyl glucoside | 2.00 |
| Polysorbate 80 | 5.00 |
| Ethylene diamine tetraacetic acid | 0.05 |
| Sodium docusate | 0.05 |
| Glycerol | 4.00 |
| Propylene glycol | 4.00 |
| Poloxamer 124 | 0.20 |
| Purified water | qs 100% |

EXAMPLE 6

Formulation of Gel Type Containing 0.1% Adapalene

| Constituents | Concentration (%) |
| --- | --- |
| Adapalene | 0.10 |
| Sodium acryloyldimethyltaurate copolymer/isohexadecane/polysorbate 80 | 3.00 |
| Aqua (and) sucrose laurate (and) alcohol | 2.00 |
| Glycerol | 4.00 |
| Ethylene diamine tetraacetic acid | 0.05 |
| Propylene glycol | 5.00 |
| Poloxamer 124 | 0.20 |
| Purified water | qs 100% |

EXAMPLE 7

Formulation of Gel Type Containing 0.3% Adapalene

| Constituents | Concentration (%) |
| --- | --- |
| Adapalene | 0.30 |
| Sodium acryloyldimethyltaurate copolymer/isohexadecane/polysorbate 80 | 3.00 |
| Aqua (and) sucrose laurate (and) alcohol | 2.00 |
| Glycerol | 5.00 |
| Ethylene diamine tetraacetic acid | 0.05 |
| Propylene glycol | 4.00 |
| Poloxamer 124 | 0.20 |
| Purified water | qs 100% |

EXAMPLE 8

Formulation of Suspension Type Containing 0.1% Adapalene

| Constituents | Concentration (%) |
| --- | --- |
| Adapalene | 0.10 |
| Bentone | 4.00 |
| Xanthan gum | 0.40 |
| Sodium acryloyldimethyltaurate copolymer/isohexadecane/polysorbate 80 | 1.00 |
| Polysorbate 80 | 5.00 |
| Decyl glucoside | 2.00 |
| Sodium docusate | 0.05 |
| Glycerol | 4.00 |
| Propylene glycol | 4.00 |
| Poloxamer 124 | 0.20 |
| Ethylene diamine tetraacetic acid | 0.05 |
| Purified water | qs 100% |

EXAMPLE 9

Formulation of Suspension Type Containing 0.1% Adapalene

| Constituents | Concentration (%) |
| --- | --- |
| Adapalene | 0.10 |
| Microcrystalline cellulose and sodium carboxymethyl cellulose | 1.50 |
| Sodium acryloyldimethyltaurate copolymer/isohexadecane/polysorbate 80 | 2.00 |
| Sucrose laurate | 3.00 |
| Glycerol | 4.00 |
| Ethylene diamine tetraacetic acid | 0.05 |
| Propylene glycol | 4.00 |
| Poloxamer 124 | 0.20 |
| Purified water | qs 100% |

EXAMPLE 10

Formulation of Suspension Type Containing 0.1% Adapalene

| Constituents | Concentration (%) |
| --- | --- |
| Adapalene | 0.10 |
| Xanthan gum | 0.40 |
| Sodium acryloyldimethyltaurate copolymer/isohexadecane/polysorbate 80 | 1.00 |
| Bentone | 4.00 |
| Aqua (and) sucrose laurate (and) alcohol | 2.00 |
| Glycerol | 4.00 |
| Ethylene diamine tetraacetic acid | 0.05 |
| Propylene glycol | 4.00 |
| Poloxamer 124 | 0.20 |
| Purified water | qs 100% |

EXAMPLE 11

Formulation of Suspension Type Containing 0.1% Adapalene

| Constituents | Concentration (%) |
| --- | --- |
| Adapalene | 0.10 |
| *Sclerotium rolfsii* | 0.70 |
| Sodium acryloyldimethyltaurate copolymer/isohexadecane/polysorbate 80 | 2.00 |
| Sucrose laurate | 3.00 |
| Sodium docusate | 0.05 |
| Glycerol | 4.00 |
| Propylene glycol | 4.00 |
| Poloxamer 124 | 0.20 |
| Ethylene diamine tetraacetic acid | 0.05 |
| Purified water | qs 100% |

EXAMPLE 12

Formulation of Suspension Type Containing 0.3% Adapalene

| Constituents | Concentration (%) |
| --- | --- |
| Adapalene | 0.30 |
| Carrageenan | 1.00 |
| Hydroxyethylcellulose | 0.30 |
| Decyl glucoside | 3.00 |
| Glycerol | 4.00 |
| Propylene glycol | 4.00 |
| Poloxamer 124 | 0.20 |
| Ethylene diamine tetraacetic acid | 0.10 |
| Purified water | qs 100% |

EXAMPLE 13

Formulation of Suspension Type Containing 0.1% Adapalene

| Constituents | Concentration (%) |
| --- | --- |
| Adapalene | 0.10 |
| Bentone | 4.00 |
| Xanthan gum | 0.40 |
| Sucrose laurate | 2.00 |
| Cocoylbetaine | 2.00 |
| Glycerol | 4.00 |
| Propylene glycol | 4.00 |
| Poloxamer 124 | 0.20 |
| Ethylene diamine tetraacetic acid | 0.05 |
| Purified water | qs 100% |

EXAMPLE 14

Formulation of Suspension Type Containing 0.1% Adapalene

| Constituents | Concentration (%) |
|---|---|
| Adapalene | 0.10 |
| Carrageenan | 1.00 |
| Hydroxyethylcellulose | 0.30 |
| Sodium lauroyl sarcosinate | 3.00 |
| Glycerol | 4.00 |
| Propylene glycol | 4.00 |
| Poloxamer 124 | 0.20 |
| Ethylene diamine tetraacetic acid | 0.10 |
| Purified water | qs 100% |

EXAMPLE 15

Formulation of Suspension Type Containing 0.1% Adapalene

| Constituents | Concentration (%) |
|---|---|
| Adapalene | 0.10 |
| Bentone | 4.00 |
| Xanthan gum | 0.40 |
| Simulgel 600PHA | 1.00 |
| Decyl glucoside | 2.00 |
| Sodium docusate | 0.05 |
| Glycerol | 4.00 |
| Propylene glycol | 4.00 |
| Poloxamer 124 | 0.20 |
| Ethylene diamine tetraacetic acid | 0.05 |
| Purified water | qs 100% |

EXAMPLE 16

Formulation of Suspension Type Containing 0.3% Adapalene

| Constituents | Concentration (%) |
|---|---|
| Adapalene | 0.30 |
| Sodium acryloyldimethyltaurate copolymer/isohexadecane/polysorbate 80 | 1.00 |
| Xanthan gum | 0.40 |
| Bentone | 4.00 |
| Aqua (and) sucrose laurate (and) alcohol | 2.00 |
| Glycerol | 4.00 |
| Propylene glycol | 4.00 |
| Poloxamer 124 | 0.20 |
| Ethylene diamine tetraacetic acid | 0.05 |
| Purified water | qs 100% |

EXAMPLE 17

Formulation of Suspension Type Containing 0.1% Adapalene

| Constituents | Concentration (%) |
|---|---|
| Adapalene | 0.10 |
| Carrageenan | 1.00 |
| Sodium acryloyldimethyltaurate copolymer/isohexadecane/polysorbate 80 | 3.00 |
| PEG-40 hydrogenated castor oil | 2.00 |
| Sodium docusate | 0.05 |
| Glycerol | 4.00 |
| Propylene glycol | 4.00 |
| Poloxamer 124 | 0.20 |
| Ethylene diamine tetraacetic acid | 0.05 |
| Purified water | qs 100% |

EXAMPLE 18

Composition in Foam Form According to the Invention

Given below are examples of foams obtained from gels and/or suspensions that are introduced into an aerosol container containing at least one propellant gas under pressure:

| Propellant gas or mixture (%) | Foam 1 Example 4 gel | Foam 2 Example 5 gel | Foam 3 Example 6 gel | Foam 4 Example 9 suspension | Foam 5 Example 10 suspension | Foam 6 Example 15 suspension |
|---|---|---|---|---|---|---|
| Propane/butane | 6 | 10 | | | | 6 |
| Propane/isobutane | | | 6 | 8 | | |
| Propane/butane/isobutane | | | | | 6 | |

The invention claimed is:

1. A composition comprising adapalene, wherein the composition is in the form of a foam and is obtained from an intermediate composition in the form of a gel or a suspension, wherein the composition comprises:
from 60% to 98% by weight relative to of the composition of a gel or a suspension, and
from 2% and 40% by weight relative to the total weight of the composition of at least one propellant gas.

2. The composition as defined by claim 1, wherein the composition has a viscosity of greater than 8,000 cps.

3. The composition as defined by claim 1, wherein the composition has a viscosity of from 8,000 cps to 32,000 cps.

4. The composition as defined by claim 1, wherein the composition comprises:
from 60% to 98% by weight relative to the total weight of the composition of an intermediate gel composition, and
from 2% to 40% by weight relative to the total weight of the composition of at least one propellant gas;
wherein said intermediate gel composition comprises, in a physiologically acceptable medium, in gel form:
adapalene,
water,
at least one gelling agent and/or pH-independent gelling agent,
at least one surfactant,
at least one wetting agent,
optionally, a chelating agent,
optionally, at least one humectant and/or emollient, and
optionally, one or more additives.

5. The composition as defined by claim 1, wherein the composition comprises:
from 60% to 98% by weight relative to the total weight of the composition of an intermediate suspension composition, and
from 2% to 40% by weight relative to the total weight of the composition of at least one propellant gas;
wherein said intermediate suspension composition comprises, in a physiologically acceptable medium, in suspension form:
adapalene,
water,
at least one gelling agent and/or pH-independent gelling agent,
optionally, one or more suspension agents,
at least one surfactant,
at least one wetting agent,
optionally, a chelating agent,
optionally, at least one humectant and/or emollient, and
optionally, one or more additives.

6. The composition as defined by claim 4, wherein the intermediate composition comprises, as a weight percentage relative to the total weight of the intermediate composition, from 0.1% to 10% of at least one gelling agent and/or pH-independent gelling agent for the aqueous phase.

7. The composition as defined by claim 4, wherein the adapalene is in dispersed form in the intermediate composition.

8. A method for treating a keratinization disorder, the method comprising administering to a subject in need thereof the composition as defined by claim 1.

9. The composition as defined by claim 4, wherein the intermediate composition comprises on a weight basis relative to the total weight of the gel or suspension:
(a) 0.01% to 5% of adapalene;
(b) 65% to 85% of water;
(c) 0.2% to 5% of at least one gelling agent and/or pH-independent gelling agent for the aqueous phase;
(d) 0% to 5% of at least one suspension agent and/or viscosity enhancer;
(e) 0.5% to 10% of at least one surfactant;
(f) 0.1% to 8% of at least one wetting agent;
(g) 0% to 1% of a chelating agent;
(h) 0% to 15% of at least one humectant and/or emollient; and
(i) 0% to 15% of one or more additives.

10. The composition as defined by claim 9, wherein the content of surfactant (e) is from 2% to 10% by weight relative to the total weight of the intermediate composition.

11. The composition as defined by claim 4, wherein the intermediate gel composition is present in an amount from 80% to 96% by weight relative to the total weight of the composition.

12. The composition as defined by claim 4, wherein the at least one propellant gas is present in an amount from 4% to 20% by weight relative to the total weight of the composition.

13. The composition as defined by claim 5, wherein the intermediate suspension composition is present in an amount from 80% to 96% by weight relative to the total weight of the composition.

14. The composition as defined by claim 5, wherein the at least one propellant gas is present in an amount from 4% to 20%.

15. The composition as defined by claim 5, wherein the intermediate suspension composition comprises as a weight percentage relative to the total weight of the intermediate composition, 0.1% to 10% of at least one gelling agent and/or pH-independent gelling agent for the aqueous phase.

16. The composition as defined by claim 15, wherein the at least one gelling agent and/or pH independent gelling agent is present in the intermediate suspension composition in an amount of from 0.2% to 5% by weight relative to the total weight of the intermediate suspension composition.

17. The composition as defined by claim 5, wherein the adapalene is in dispersed form in the intermediate composition.

18. The composition of claim 6, wherein the at least one gelling agent and/or pH-independent gelling agent is present in the intermediate composition in an amount from 0.2% to 5% by weight relative to the total weight of the intermediate composition.

19. The method as defined by claim 8, wherein the keratinization disorder is acne.

20. The composition in gel form as defined by claim 9, wherein the content of surfactant (e) is from 2% to 10% by weight relative to the total weight of the intermediate composition.

21. The composition as defined by claim 5, wherein the intermediate composition comprises on a weight basis relative to the total weight of the gel or suspension:
(a) 0.01% to 5% of adapalene;
(b) 65% to 85% of water;
(c) 0.2% to 5% of at least one gelling agent and/or pH-independent gelling agent for the aqueous phase;
(d) 0% to 5% of at least one suspension agent and/or viscosity enhancer;
(e) 0.5% to 10% of at least one surfactant;
(f) 0.1% to 8% of at least one wetting agent;
(g) 0% to 1% of a chelating agent;
(h) 0% to 15% of at least one humectant and/or emollient; and
(i) 0% to 15% of one or more additives.

* * * * *